(12) United States Patent
Wei et al.

(10) Patent No.: US 8,007,854 B2
(45) Date of Patent: Aug. 30, 2011

(54) CERAMIC COATING AND METHOD OF PREPARATION THEREOF

(75) Inventors: Mei Wei, Coventry, CT (US); Haibo Qu, Storrs, CT (US); Xiaohua Yu, Willimantic, CT (US)

(73) Assignee: The University of Connecticut, Farmington, CT (US)

( * ) Notice: Subject to any disclaimer, the term of this patent is extended or adjusted under 35 U.S.C. 154(b) by 246 days.

(21) Appl. No.: 11/619,659

(22) Filed: Jan. 4, 2007

(65) Prior Publication Data
US 2007/0184299 A1 Aug. 9, 2007

Related U.S. Application Data

(60) Provisional application No. 60/756,039, filed on Jan. 4, 2006, provisional application No. 60/828,472, filed on Oct. 6, 2006, provisional application No. 60/848,045, filed on Sep. 27, 2006.

(51) Int. Cl.
*A61L 33/00* (2006.01)

(52) U.S. Cl. ...... 427/2.1; 427/2.25; 427/2.26; 427/2.27; 623/1.15

(58) Field of Classification Search ............... 428/323; 427/2.27, 2.25
See application file for complete search history.

(56) References Cited

U.S. PATENT DOCUMENTS

| | | | |
|---|---|---|---|
| 5,205,921 A | 4/1993 | Shirkanzadeh | |
| 6,136,369 A * | 10/2000 | Leitao et al. | 427/2.27 |
| 6,139,585 A | 10/2000 | Li | |
| 6,207,218 B1 | 3/2001 | Layrolle et al. | |
| 6,569,489 B1 | 5/2003 | Li | |
| 7,087,086 B2 | 8/2006 | Li et al. | |
| 2002/0018797 A1 | 2/2002 | Cui et al. | |
| 2006/0204491 A1 | 9/2006 | Kakubo et al. | |
| 2006/0216494 A1 * | 9/2006 | Furedi-Milhofer et al. | 428/323 |

FOREIGN PATENT DOCUMENTS

| | | |
|---|---|---|
| EP | 1566186 A1 | 8/2005 |
| WO | 2004024201 A2 | 3/2004 |
| WO | 2004040036 A1 | 5/2004 |
| WO | 2004040037 A1 | 5/2004 |

OTHER PUBLICATIONS

H. Qu and M. Wei, "The Effect of Temperature and Initial pH on Biomimetic Apatite Coating", Journal of Biomedical Materials Research: 87B, 204-212 (2008.
X. Yu, H. Qu, D.A. Knecht, and M. Wei, "Incorporation of Bovine Serum Albumin into Biomimetic Coatings on Titanium with High Loading Efficacy and Its Release Behavior", Journal of Materials Science, Materials in Medicine, DOI 10.1007/s10856-008-3571-6, 2008.
The International Searching Authority, International Search Report, PCT/US2007/000092, Date of mailing: Aug. 6, 2008, 6 pages.
The International Searching Authority, Written Opinion, PCT/US2007/000092, Date of mailing: Aug. 6, 2008, 9 pages.

(Continued)

*Primary Examiner* — Michael Barr
*Assistant Examiner* — Andrew Bowman
(74) *Attorney, Agent, or Firm* — Cantor Colburn LLP

(57) ABSTRACT

A ceramic coating with gradient density/porosity and/or incorporated biologically active agents can be fabricated on the surface of substrates, including the surface of implantable medical devices.

11 Claims, 7 Drawing Sheets

OTHER PUBLICATIONS

Foreign Document No. 1451444 CN, Publication date: Oct. 29, 2003, Abstract 1 page.
Foreign Document No. 1528468 CN, Publication date: Sep. 15, 2004, Abstract 1 page.
Foreign Document No. 2002000698 BR, Publication date: Aug. 24, 2004, Abstract 1 page.
Kim H-M, Miyaji F, Kokubo T, Nakamura T, "Bonding strength of bonelike apatite layer to Ti metal substrate", Journal of Biomedical Materials Research, 1997, 38(2): 121-127, Abstract 1 page.
Y. Liu et al., "Biomimetic coprecipitation of calcium phosphate and bovine serum albumin on titanium alloy", J. Biomed. Mater. Res., 57:327-335, 2001, Abstract 1 page.
Yanli et al., Formation of bonelike apatite-collagen composite coating on the surface of NiTi shape memory alloy, Scripta Materialia 54 (2006) 89-92.
Gross et al., The Heat Precipitation of Collagen from Neutral Salt Solution: Some Rate-Regulating Factors, The Journal of Biological Chemistry, vol. 233, No. 2, 355-360, Jan. 16, 1958.
Qu et al., Improvement of Bonding Strength Between Biomimetic Apatite Coating and Substrates, Part B: Applied Biomaterials: vol. 84B Issue 2, pp. 436-443 2007.
Qu et al., The Effect of Initial pH on Morphology of Biomimetic Apatite Coating, Key Engineering Materials vols. 330-332 (2007), pp. 757-760.
Kim et al., Bonding strength of bonelike apatite layer to Ti metal substrate, Journal of Biomedical Materials Research 1997, 38(2): 121-127; Abstract Only (1 page).
Barrere et al., Nucleation of biomimetic Ca—P coatings on Ti6A14V from a SBFx5 solution: influence of magnesium, Biomaterials 23 (2002) 2211-2220.
Barrere et al., Influence of ionic strength and carbonate on the Ca—P coating formation from SBFx5 solution, Biomaterials 23 (2002) 1921-1930.
U.S. Appl. No. 12/265,979, filed Nov. 6, 2008.
U.S. Appl. No. 12/265,956, filed Nov. 6, 2008.
Chen et al., Biomimetic coating of apatite/collagen composite on Poly L-lactic Acid facilities cell seeding. Conf. Proc. IEEE Eng. Med. Biol. Soc. 2005, vol. 4, pp. 4087-4090, Abstract, 1 page.
International Search Report; International Application No. PCT/US2008/082616; International Filing Date Jun. 11, 2008; 7 pages.
Written Opinion of the International Searching Authority; International Search Report; International Application No. PCT/US2008/082616; International Filing Date Jun. 11, 2008; 8 pages.

* cited by examiner

CERAMIC COATING AND METHOD OF PREPARATION THEREOF

CROSS-REFERENCE TO RELATED APPLICATIONS

This application claims the benefit of U.S. Patent Application Ser. No. 60/756,039, filed Jan. 4, 2006; U.S. Patent Application Ser. No. 60/828,472, filed Oct. 6, 2006; and U.S. Patent Application Ser. No. 60/848,045, filed Sep. 27, 2006; each of which is incorporated by reference herein in its entirety.

STATEMENT REGARDING FEDERALLY SPONSORED RESEARCH

The U.S. Government has certain rights in this invention pursuant to Grant No. 0500269 awarded by the National Science Foundation.

BACKGROUND OF INVENTION

Implantable medical devices, such as orthopedic and dental prostheses, can be made more permanent if the interface between the existing bone and the device contains some natural bone growth to knit the two components together. Such ingrowth has advantages over the use of bone cement, both in terms of stability and permanency.

"Bioactive" coatings on implantable medical devices allow for the ingrowth of natural bone into and around the device, forming chemical bonds between the device and natural bone. Calcium-phosphate coatings have been prepared and have been shown to promote direct bone apposition.

There are a variety of approaches to prepare a bioactive ceramic coating on a substrate, for example electrophoresis, plasma spray method, and the so-called biomimetic method. Several of these approaches have their drawbacks, however. The electrophoresis method, although a low-temperature coating technique, results in a relatively low bond strength at the interface between the coating and the substrate. Therefore, a post-sintering step is usually necessary. The plasma spraying method does provide a relatively strong bond, however due to the high temperatures involved in this method, the hydroxyapatite coating decomposes during the coating process. The biomimetic method results in carbonated nanocrystalline apatite that is chemically bonded to a substrate through the process of immersing the substrate in an aqueous solution containing calcium, phosphate, and carbonate ions. Other ions, such as sodium, potassium, magnesium, chloride, sulfate, and silicate, may optionally be present in the solution.

The coatings achieved by previously disclosed methods, however, do not have a gradient structure.

There have been attempts to incorporate different proteins into the biomimetic apatite coatings by mixing the proteins with the biomimetic coating solutions. However, only up to forty-five percent of the protein in the solution could be incorporated into the coating using the biomimetic method.

There remains a need in the art for improved bioactive ceramic coatings in addition to processes to prepare such coatings. There also remains a need in the art to improve the protein incorporation efficiency into apatite coatings.

BRIEF DESCRIPTION OF THE INVENTION

Disclosed herein is a method of coating a substrate with a gradient ceramic coating comprising exposing a portion of a substrate to an aqueous system at a temperature of about 20° C. to about 100° C. to form a gradient ceramic coating on a surface of the substrate; wherein the aqueous system comprises water, $Ca^{2+}$, $Mg^{2+}$, $Na^+$, $K^+$, $Cl^-$, $SO_4^{2-}$, $HPO_4^{2-}$, $HCO_3^-$ and a buffer system; and wherein the aqueous system has an initial pH of about 5.5 to about 7.5.

In another embodiment, a coated substrate comprises a gradient ceramic coating, wherein the gradient ceramic coating is prepared by exposing a portion of a substrate to an aqueous system; wherein the aqueous system comprises water, $Ca^{2+}$, $Mg^{2+}$, $Na^+$, $K^+$, $Cl^-$, $SO_4^{2-}$, $HPO_4^{2-}$, $HCO_3^-$ and a buffer system.

In another embodiment, a method of incorporating a biologically active agent into a ceramic coating on a substrate comprises exposing a portion of a substrate to an aqueous system at a temperature of about 20° C. to about 100° C. to form ceramic coating on a surface of the substrate; wherein the aqueous system comprises water, $Ca^{2+}$, $Mg^{2+}$, $Na^+$, $K^+$, $Cl^-$, $SO_4^{2-}$, $HPO_4^{2-}$, $HCO_3^-$, a buffer system, and a biologically active agent; wherein the aqueous system has an initial pH of about 5.5 to about 7.5; wherein the ratio of aqueous system volume to the substrate surface area is about 5 to 50 mm; and wherein the biologically active agent concentration in the aqueous system is less than about 1 mg/ml.

In yet another embodiment, a coated substrate comprises a ceramic coating comprising a biologically active agent, wherein the ceramic coating is prepared by exposing a portion of a substrate to an aqueous system, wherein the exposing is performed at a temperature of about 20° C. to about 100° C.; wherein the aqueous system comprises water, $Ca^{2+}$, $Mg^{2+}$, $Na^+$, $K^+$, $Cl^-$, $SO_4^{2-}$, $HPO_4^{2-}$, $HCO_3^-$, a buffer system and a biologically active agent; and wherein the aqueous system has an initial pH of about 5.5 to about 7.5.

In still another embodiment, a reactor for coating a substrate with a bioactive ceramic coating comprises a liquid-holding container with a volume sufficient to allow a ratio of the aqueous system volume to the substrate surface area to be about 5 to about 50 mm; and a gas valve to control the rate of release of a gas from the container.

DETAILED DESCRIPTION

Figure 1:
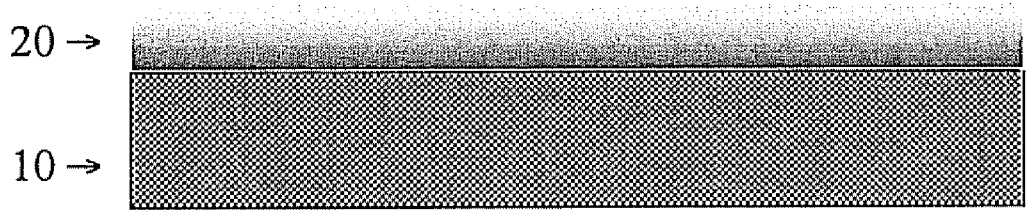
FIG. 1 illustrates a schematic of a gradient coating (20) on a substrate (10).

Disclosed herein are methods of forming gradient ceramic coatings and/or ceramic coatings containing biologically active agents; coatings prepared therefrom; and articles prepared therefrom.

The methods described herein allow for a mild and convenient approach to form a gradient ceramic coating or apatite coating on the surface of a variety of substrates. The methods involve immersing a substrate or portion of a substrate into an aqueous system under controlled conditions of temperature, pH, ion concentration, and buffer to result in the formation of a gradient ceramic coating or a bone-like apatite layer on the substrate surface. The gradient morphology improves the bioactivity of the ceramic coating, as the portion of the coating in direct contact with the substrate is dense, allowing a strong bond to be formed between the coating and substrate. The surface portion of the ceramic coating is less dense/more porous. When used in implantable medical device applications, the porous surface allows for bone ingrowth as bone cells can penetrate the porous coating surface to form a strong bond between the substrate and existing bone.

Also disclosed herein is a method of coating a substrate with a ceramic coating comprising a biologically active agent. The advantage of the present method is that biologically active agent can be co-precipitated with apatite crystals onto a substrate without losing its biological activity. In addition, the biodegradation of these biomimetic coatings in vivo can lead to gradual release of the incorporated biologically active agents. As a result, these coatings have great potential as drug-carriers in orthopedic and dental applications.

Furthermore, the methods described herein allow for a mild and convenient approach to incorporate biologically active molecules into a ceramic coating or apatite coating on the surface of a variety of substrates. A significant amount (about 50 to 100%) of the biologically active agent is incorporated into the ceramic coating. The methods involve immersing a substrate or a portion of a substrate into an aqueous system containing biologically active agent under controlled conditions of temperature, pH, ion concentration, and buffer to result in the formation of a ceramic coating or a bone-like apatite layer on the substrate surface containing significant amounts of the biologically active agent. When used in implantable medical device applications, the ceramic coating allows for strong bone fixation quickly. Furthermore, the biologically active agents can aid the regeneration and healing of bone tissue.

The method of incorporating biologically active agents into a ceramic coating on a substrate with high yield and high efficiency comprises exposing a portion of a substrate to an aqueous system to form a ceramic coating on a surface of the substrate; wherein the aqueous system comprises water, $Ca^{2+}$, $Mg^{2+}$, $Na^+$, $K^+$, $Cl^-$, $SO_4^{2-}$, $HPO_4^{2-}$, $HCO_3^-$, a biologically active agent, and a buffer system. In general, the ratio of the aqueous system volume to the substrate surface area is about 5 to about 50 mm in order to achieve about 50 to about 100% incorporation efficiency of the biologically active agent in the coating. The concentration of the biologically active agent in the aqueous system is less than about 1.0 mg/ml, specifically less than about 0.75 mg/ml, and more specifically less than about 0.5 mg/ml. The initial pH and the concentration of buffer in the aqueous system are selected and controlled in order to produce the desired bioactive ceramic coating.

As used herein "exposing a portion of a substrate" means any portion or all of the substrate is exposed to the aqueous system.

As used herein "biologically active agent" means an active pharmaceutical ingredient (e.g. an antibiotic) or other biologically active molecule such as a protein (e.g. a growth factor, osteoclacin, etc.), a gene, an osteogenic factor, a mitogen, and the like.

As used herein "ratio of the aqueous system volume to the substrate surface area" means the volume of the aqueous system in x unit of length cubed divided by the substrate surface area in x unit of length squared. For example for a 5 millimeter×5 millimeter square substrate exposed to a 5 milliliter (5 milliliters=5000 cubic millimeters) volume of aqueous system would have a ratio of the aqueous system volume to the substrate surface area of 200=length in millimeters.

In another embodiment, a ceramic coating contains a biologically active agent, wherein the efficiency of the incorporation of the biologically active agent from the aqueous system into the ceramic coating is greater than 50%.

The coating methods are performed at low temperatures suitable for temperature sensitive substrates such as polymeric materials and hydrogels, or temperature sensitive biologically active agents. The coating process can be performed at a relatively short amount of time. Furthermore, the methods can be used to coat porous substrates and substrates having complex geometries. Additional embodiments are directed to the ceramic coatings themselves as well as articles prepared from substrates comprising the ceramic coatings. In general, the ceramic coating can be prepared by exposing a portion of a substrate to an aqueous system comprising inorganic ions. The substrate is exposed for a period of time and at a temperature to allow for the formation of the ceramic coating on the exposed surface of the substrate. Exposing can include immersion of the substrate or portion of the substrate to the aqueous system. The resulting ceramic coating is generally a bone-like apatite.

The aqueous system generally comprises the following inorganic ions: $Ca^{2+}$, $Mg^{2+}$, $Na^+$, $K^+$, $Cl^-$, $SO_4^{2-}$, $HPO_4^{2-}$ and $HCO_3^-$. The aqueous system can be prepared by dissolving in an aqueous solvent salts that when disassociated will result in the particular ions $Ca^{2+}$, $Mg^{2+}$, $Na^+$, $K^+$, $Cl^-$, $SO_4^{2-}$, $HPO_4^{2-}$ and $HCO_3^-$. The aqueous solvent can be deionized and purified water. Exemplary salts include those that result in an aqueous solution of the desired ions, for example, alkali metal halides, alkaline earth metal halides, alkali metal hydrogen carbonates, alkali metal phosphates, and alkali metal sulfates. Specific salts include, NaCl, KCl, $K_2HPO_4$, $MgCl_2$, $Na_2SO_4$, $CaCl_2$ and $NaHCO_3$.

The particular concentrations of each of the above-described ions initially present in the aqueous system can be as follows:

$Ca^{2+}$ at about 2.5 to about 15.0 mM, specifically about 4.0 to about 12.0, and more specifically about 8.0 to about 10.0 mM;

$Mg^{2+}$ at about 0.5 to about 5.0 mM, specifically about 1.0 to about 4.5 mM, and more specifically about 1.5 to about 3.0 mM;

$Na^+$ at about 50.0 to about 300.0 mM, specifically about 80.0 to about 200.0 mM, and more specifically about 100.0 to about 150.0 mM;

$K^+$ at about 2.0 to about 20.0 mM, specifically about 5.0 to about 15.0 mM, and more specifically about 7.0 to about 10.0 mM;

$Cl^-$ at about 50.0 to about 350.0 mM, specifically about 100.0 to about 200.0 mM, and more specifically about 120.0 to about 150.0 mM;

$SO_4^{2-}$ at about 0 to about 2.0 mM, specifically about 0.1 to about 1.0 mM, and more specifically about 0.2 to about 0.5 mM;

$HPO_4^{2-}$ at about 1.0 to about 10.0 mM, specifically about 3.0 to about 8.0 mM, and more specifically about 5.0 to about 7.5 mM; and $HCO_3^-$ at about 5.0 to about 100.0 mM, specifically about 10.0 to about 50.0 mM, and more specifically about 20.0 to about 40.0 mM.

In one embodiment, the particular concentrations of ions initially present in the aqueous system can be as follows: $Ca^{2+}$ is present in an amount of about 4.0 to about 12.0 mM; $Mg^{2+}$ is present in an amount of about 1.0 to about 4.5 mM; $Na^+$ is present in an amount of about 80.0 to about 200.0 mM; $K^+$ is present in an amount of about 5.0 to about 15.0 mM; $Cl^-$ is present in an amount of about 100.0 to about 200.0 mM; $SO_4^{2-}$ is present in an amount of about 0.1 to about 1.0 mM; $HPO_4^{2-}$ is present in an amount of about 3.0 to about 8.0 mM; and $HCO_3^-$ is present in an amount of about 10.0 to about 50.0 mM.

In another embodiment, the particular concentrations of ions initially present in the aqueous system can be as follows: $Ca^{2+}$ is present in an amount of about 8.0 to about 10.0 mM; $Mg^{2+}$ is present in an amount of about 1.5 to about 3.0 mM; $Na^+$ is present in an amount of about 100.0 to about 150.0 mM; $K^+$ is present in an amount of about 7.0 to about 10.0 mM; $Cl^-$ is present in an amount of about 120.0 to about 150.0 mM; $SO_4^{2-}$ is present in an amount of about 0.2 to about 0.5 mM; $HPO_4^{2-}$ is present in an amount of about 5.0 to about 7.5 mM; and $HCO_3^-$ is present in an amount of about 20.0 to about 40.0 mM.

An additional component present in the aqueous system is a buffer system. The buffer system can contain HEPES (4-(2-hydroxyethyl)-1-piperazineethanesulfonic acid or N-2-hydroxyethylpiperazine-N'-2-ethanesulfonic acid; Molecular formula: $C_8H_{17}N_2SO_3$; CAS No: 7365-45-9) and an alkali metal hydrogen carbonate (e.g. $NaHCO_3$, KHCO3, etc.) which are added to the aqueous system in amounts to substantially stabilize the aqueous system. The concentration of HEPES present in the aqueous system can be at about 5.0 grams per liter (g/L) to about 80.0 g/L, specifically about 10.0 g/L to about 60.0 g/L, and more specifically about 12.0 g/L to about 48.0 g/L.

Additional buffer systems are also suitable and can be tailored to provide a desired property of the coating, which in some cases is a gradient morphology. The additional buffer system may include tris-hydroxymethyl aminomethan (TRIS), HEPES salts, piperazine-1,4-bis(2-ethanesulfonic acid) (PIPES), PIPES salts, combinations of the foregoing with an alkali metal carbonate, and combinations thereof.

In one embodiment, the buffer system is not a carbonate-bicarbonate buffer system prepared by bubbling carbon dioxide into the aqueous system.

In another embodiment, the aqueous system is stable and no visual precipitation occurs throughout the coating formation.

The aqueous system may optionally contain additional ionic components such as silicate, strontium, zinc, silver, fluoride, combinations thereof, and the like.

FIG. 1 illustrates a schematic of a gradient ceramic coating (20) on a substrate (10). The coating nearest the substrate surface has a greater density and lower porosity as compared to the density/porosity of the surface of the ceramic coating. As previously mentioned, the dense coating at the interface with the substrate provides a strong bond between the coating and the substrate. The more porous surface of the ceramic coating, when present on implantable medical devices for example, will induce bone ingrowth and thereby will integrate with the natural bone when implanted in a patient. As such, the ceramic coatings having a gradient density/porosity can be considered bioactive.

As used herein, "gradient ceramic coating" means a progressively increasing or decreasing difference in the density or porosity of the ceramic coating over the distance of the thickness of the coating.

As used herein, the term "functionally gradient bioactive ceramic coating" means the dense coating at the interface will provide a strong bonding strength with the substrate, while the porous portion at the surface will induce bone ingrowth and thereby well integrate with the natural bone.

As used herein "bioactive" means the ceramic coating can induce bone ingrowth resulting in the formation of a strong bond across the interface between the coating and the natural bone.

The density/porosity of the ceramic coating can be adjusted by several parameters including amount of $NaHCO_3$, initial pH of the aqueous system, amount of buffer, temperature of the coating process, calcium concentration, and phosphate concentration.

The density/porosity of the ceramic coating can be adjusted by carefully choosing the initial pH of the aqueous system. Over time, the pH of the aqueous system increases due to the bicarbonate ions in the solution naturally decomposing into hydroxyl groups and carbon dioxide. The initial formation of the gradient coating is formed when the aqueous system has an initial pH of about 5.5 to about 7.5. The initial stage of the coating process is slower as $HCO_3^-$ inhibits the crystal growth of the coating. Therefore, the coating will grow slower and denser at the initial stages of the coating process as the concentration $HCO_3^-$ is initially high. As the $HCO_3^-$ ions decompose, the rate of coating formation increases and the inhibitory effect of the bicarbonate ions is less pronounced. The increased rate of coating formation results in the gradient morphology.

The amount of buffer in the aqueous system will also alter the pH change profile during the coating process. When there is less buffer in the aqueous system, more $HCO_3^-$ will be present in the system when the pH range for apatite formation is achieved. In the absence of buffer in the aqueous system, the coating that forms exhibits minimal gradient morphology, as the density/porosity of the resulting coating is substantially the same throughout the entire thickness of the coating.

The calcium and phosphate concentrations can also be chosen to obtain the optimal pH range for apatite formation.

If needed, the initial pH of the aqueous system can be adjusted by the addition of an inorganic acid or inorganic base. An exemplary inorganic acid includes halo acids (e.g. hydrochloric acid). Exemplary inorganic bases include alkali metal hydroxides (e.g. NaOH, KOH, etc.). The initial pH of the aqueous system can be about 5.5 to about 7.5, specifically about 6.0 to about 6.60, more specifically about 6.10 to about 6.45, and yet more specifically about 6.20 to about 6.38. As used herein, "initial pH" means the pH of the aqueous system prior to contact with the substrate to be coated.

The initial pH of the aqueous system and the type and amount of buffer system can be selected to generate a desired gradient ceramic coating. After the desired aqueous system is prepared, the substrate is exposed to the aqueous system at a particular temperature to allow for the formation of the gradient coating. The substrate can be exposed to the aqueous system for a time sufficient for the formation of a gradient coating of sufficient thickness. Coatings having sufficient thickness can be formed in less than about 3 days. Specifically, the substrate can be exposed in the aqueous system for about 4 to about 48 hours, specifically about 10 to about 40 hours, more specifically about 12 to about 35 hours, and yet more specifically about 20 to about 30 hours until the desired thickness of coating is formed.

To prepare a ceramic coating comprising a biologically active agent the substrate can be exposed to the aqueous system for a time sufficient for the formation of a coating of sufficient thickness. Coatings having sufficient thickness can be formed in less than about 3 days. Specifically, the substrate can be exposed in the aqueous system for about 4 to about 48 hours, specifically about 10 to about 40 hours, more specifically about 12 to about 35 hours, and yet more specifically about 20 to about 30 hours until the desired thickness of coating is formed.

The temperature of the aqueous system during the coating process can be about 20 to about 100° C., more specifically about 25 to about 60° C., yet more specifically about 35 to about 45° C., and still yet more specifically about 38 to about 42° C. In one embodiment, the temperature of the aqueous system can be varied during the coating process to create a gradient coating. At different temperatures, the optimal pH range for apatite formation will also be different as the rate of $HCO_3^-$ decomposition is affected by temperature. By increasing the temperature, the greater the rate of $HCO_3^-$ decomposition as compared to lower temperatures for same time period.

In one embodiment, a gradient coating can be formed from an aqueous system containing about 18 mM $NaHCO_3$, 12.5 mM $Ca^+$, 5 mM $HPO_4^{2-}$, and 44 g/L HEPES. The initial pH of the aqueous system is about 6.02 and the coating process performed at a temperature of about 42° C.

In another embodiment, the temperature of the aqueous system during the coating process can be about 20 to about 100° C., the initial pH of about 5.5 to about 7.5, the $HCO_3^-$ at about 10 to about 150 mM, $HPO_4^{2-}$ at about 1 to about 10 mM, $Ca^{2+}$ at about 2.5 to about 15 mM, and HEPES at about 5 g/L to about 80 g/L.

In yet another embodiment, the temperature of the aqueous system during the coating process can be about 25 to about 60° C., the initial pH is about 5.5 to about 7.5, $HCO_3^-$ at about 20 to about 100 mM, $HPO_4^{2-}$ at about 3 to about 8 mM, $Ca^{2+}$ at about 4 to about 13 mM, and HEPES at about 10 g/L to about 50 g/L.

In yet another embodiment, the temperature of the aqueous system during the coating process can be about 35 to about 45° C., the initial pH is about 6.38 to about 6.45, $HCO_3^-$ at about 30 to about 40 mM, $HPO_4^{2-}$ at about 2.5 to about 3.5 mM, $Ca^{2+}$ at about 7 to about 9 mM, and HEPES at about 10 g/L to about 14 g/L.

In still yet another embodiment, the temperature of the aqueous system during the coating process can be about 35 to about 45° C., the initial pH is about 6.00 to about 6.10, $HCO_3^-$ at about 60 to about 80 mM, $HPO_4^{2-}$ at about 4.5 to about 5.5 mM, $Ca^{2+}$ at about 11 to about 13 mM, and HEPES at about 42 g/L to about 45 g/L.

In one embodiment, the gradient coating has a density of about 75 to about 90% closest to the substrate while the surface of the coating away from the substrate has a density of about 35 to about 60%, which is demonstrated by scanning electron microscope (SEM) observations.

In another embodiment, the coating has a density of about 50 to about 90%, specifically about 65 to about 85%, and more specifically about 70 to about 80%.

Generally, the longer the substrate is exposed to the aqueous system, the thicker the resulting ceramic coating will be. Coatings having a total thickness of about 0.1 to about 70 micrometers can be formed, specifically about 1 to about 50 micrometers, yet more specifically about 5 to about 40 micrometers, and still yet more specifically about 10 to about 25 micrometers. The crystal size of the resulting coating is less than about 1 micrometer.

In one embodiment, the coating has a bonding strength between the coating and the substrate of about 5 to about 25 MPa as determined using a modified ASTM C-633 method as provided in Kim H-M, Miyaji F, Kokubo T, Nakamura T. "Bonding strength of bonelike apatite layer to Ti metal substrate." *Journal of Biomedical Materials Research* 1997; 38(2):121-127, which is incorporated herein in its entirety. More specifically, the bonding strength between the coating and the substrate is about 8 to about 20 MPa, and more specifically about 10 to about 19 MPa. In a further embodiment, the bonding strength between the coating and the substrate is equal to or greater than the cohesive strength within the coating.

In another embodiment, a method of coating a substrate with a gradient ceramic comprises exposing a portion of a substrate to an aqueous system in a closed system, e.g., a sealed container, at a temperature of about 20° C. to about 100° C. to form a gradient ceramic coating on a surface of the substrate, wherein the aqueous system comprises water, $Ca^{2+}$, $Mg^{2+}$, $Na^+$, $K^+$, $Cl^-$, $HPO_4^{2-}$, $HCO_3^-$ and a buffer system, wherein the aqueous system has an initial pH of about 5.5 to about 7.5, and wherein the closed system comprises a volume ratio of headspace to aqueous system of about 5 to about 15 at atmospheric pressure.

In yet another embodiment, a method of coating a substrate with a gradient ceramic comprises exposing a portion of a substrate to an aqueous system in a closed system, e.g., a sealed container, at a temperature of about 30° C. to about 60° C., specifically about 35° C. to about 45° C., to form a gradient ceramic coating on a surface of the substrate, wherein the aqueous system comprises water, 7.5 millimolar (mM) $Ca^{2+}$, 3 mM $HPO_4^{2-}$, 142.0 mM $Na^+$, 5.0 mM $K^+$, 1.5 $Mg^{2+}$, 103.0 mM $Cl^-$, 27.0 mM $HCO_3^-$, and 0.5 mM $SO_4^{2-}$, HEPES (11.928 g per 1000 ml water), and 1M HCl (6.5 ml per 1000 ml water), and wherein the closed system comprises a volume ratio of headspace to aqueous system of about 5 to about 15 at atmospheric pressure.

When preparing a ceramic coating containing a biologically active agent, the incorporation efficiency of the biologically active agent into the ceramic coating can be adjusted by carefully choosing the ratio of aqueous system volume to substrate surface area for the coating process. When substrates are soaked in the aqueous system, both $Ca^{2+}$ and $HPO_4^{2-}$ ions are adsorbed onto the surface of the substrate to form apatite coatings. The bicarbonate ($HCO_3^-$) ion in the solution has a two-fold function. These ions act as an inhibitor to slow down the apatite formation while at the same time, they decompose into $CO_2$ and $OH^-$ during the coating process, as shown in equation (1).

$$HCO_3^- \rightarrow CO_2 + OH^- \qquad (1)$$

By carefully controlling both the ratio of aqueous system volume to substrate surface area and the $HCO_3^-$ decomposition rate (the $CO_2$ release rate), the amount of calcium and phosphate ions depositing on the surface of the substrate can be maximized while minimizing the amount of $HCO_3^-$ remaining in the aqueous system. The coating formation process can be expedited by the depletion of $HCO_3^-$. As the apatite has a strong affinity for the biologically active agent, the more apatite is formed, the greater the amount of biologically active agent that can be incorporated into the ceramic coating.

To achieve a high efficiency of the incorporation of the biologically active agent in the ceramic coating, the ratio of aqueous system volume to substrate surface area for the coating process can be about 1 to about 50, specifically about 4 to about 40, more specifically about 5 to about 30, and yet more specifically about 10 to about 20 mm.

The efficiency of the incorporation of the biologically active agent from the aqueous system into the ceramic coating can be about 50% or greater, specifically about 60% or greater, more specifically about 70% or greater, and yet more specifically about 75% or greater.

The temperature of the aqueous system during the coating process to form the ceramic coating containing a biologically active agent can be about 20 to about 100° C., more specifically about 25 to about 60° C., yet more specifically about 35 to about 45° C., and still yet more specifically about 38 to about 42° C. At different temperatures, the optimal pH range and aqueous system volume for apatite formation will also be different as the rate of $HCO_3^-$ decomposition is affected by temperature and aqueous system volume. By increasing the temperature, the greater the rate of $HCO_3^-$ decomposition will be increased as compared to lower temperatures for same time period.

In another embodiment, the temperature of the aqueous system during the coating process to form a ceramic coating containing a biologically active agent can be about 20 to about 100° C., the initial pH can be about 5.5 to about 7.5, the $HCO_3^-$ at about 10 to about 150 mM, $HPO_4^{2-}$ at about 1 to about 10 mM, $Ca^{2+}$ at about 2.5 to about 15 mM, and HEPES at about 5 g/L to about 80 g/L.

In yet another embodiment, the temperature of the aqueous system during the coating process to form a ceramic coating containing a biologically active agent can be about 25 to about 60° C., the initial pH can be about 5.5 to about 7.5, $HCO_3^-$ at about 20 to about 100 mM, $HPO_4^{2-}$ at about 3 to about 8 mM, $Ca^{2+}$ at about 4 to about 13 mM, and HEPES at about 10 g/L to about 50 g/L.

In yet another embodiment, the temperature of the aqueous system during the coating process to form a ceramic coating containing a biologically active agent can be about 35 to about 45° C., the initial pH can be about 6.38 to about 6.45, $HCO_3^-$ at about 30 to about 40 mM, $HPO_4^{2-}$ at about 2.5 to about 3.5 mM, $Ca^{2+}$ at about 7 to about 9 mM, and HEPES at about 10 g/L to about 14 g/L.

In yet another embodiment, the biologically active agent incorporation efficiency is above 80% when the biologically active agent concentration in the aqueous system is less than 0.1 mg/ml.

In still yet another embodiment, the temperature of the aqueous system during the coating process to form a ceramic coating containing a biologically active agent can be about 35 to about 45° C., the initial pH is about 6.00 to about 6.10, $HCO_3^-$ at about 60 to about 80 mM, $HPO_4^{2-}$ at about 4.5 to about 5.5 mM, $Ca^{2+}$ at about 11 to about 13 mM, and HEPES at about 42 g/L to about 45 g/L.

Exemplary substrates that can be coated with the described ceramic coating include implantable medical devices useful in biomedical applications, including orthopedic applications (e.g., joint prostheses) and devices and appliances for orthodontic applications and dental implants. The aqueous system lends itself to the uniform application of a ceramic coating even to substrates having surfaces of complex geometries. Additional applications in the biomedical field include drug/protein delivery devices. In addition, this coating system can also be used to load living cells.

The coatings can be used to prepare medical, surgical, reconstructive, orthopedic, orthodontic, prosthodontic, endodontic or dental devices, implants, appliances, or a component thereof (e.g., a screw or other attaching connector, etc.).

The substrates can be made from a wide variety of material types, including metal, ceramic, polymeric materials, silicon, glass, and the like. When used in biomedical applications, the material should be biocompatible. As used herein, "biocompatible" means being biologically compatible in that a toxic, injurious, or immunological response is not produced in living tissue. Suitable material for the substrate includes, for example, titanium, stainless steel, nickel, cobalt, niobium, molybdenum, zirconium, tantalum, chromium, alloys thereof and combinations thereof. Exemplary polymeric material include polylactide (PLA), poly(glycolic acid) (PGA), poly (methyl methacrylate) (PMMA), other biocompatible polymeric material, and the like. Exemplary ceramic materials include alumina, titania, and zirconia, glasses, and calcium phosphates, such as hydroxyapatite and tricalcium phosphate.

Prior to the coating step, the surface of the substrate can be prepared to improve the adhesion of the coating. The substrate can be cleaned or treated to remove any surface contaminants. The metal substrates can be surface treated by sand-blasting, scoring, polishing, and grinding to increase the surface roughness. Alternatively, the metal substrate can undergo chemical surface treatments prior to coating to provide a level of surface roughness. Exemplary chemical treatments for metal substrates include, acid etchings with strong mineral acids, such as hydrofluoric, hydrochloric, sulfuric, nitric and perchloric acids; treatment with strong alkalis, such as sodium hydroxide, potassium hydroxide; treatment with oxidizing agents such as peroxyhalogen acids, hydroxyperoxides, or hydrogen peroxide to form a metal oxide layer. Washing with deionized or purified water can effect removal of surface contaminants due to the surface treatment.

In one embodiment, the coating methods described herein do not involve bubbling carbon dioxide or a gaseous weak acid into the aqueous system to control the pH of the aqueous system.

Although the coatings have been discussed in terms of its application for implantable medical devices, the coatings can be used for a wide variety of uses, such as a hydroxyapatite chromatography sorbent useful for the separation of biomolecules, for example.

Also disclosed herein is a reactor for coating a substrate with a bioactive ceramic coating comprising a liquid-holding container and a gas valve ("pressure valve") to control the rate of release of a gas from the container. The liquid-holding container can be prepared from a non-reactive or inert material such as glass or Teflon™.

The shape of the interior of the liquid-holding container can be a regular shape such as a cube, a cone, a sphere, a cylinder, or the like. Optionally, the shape of the interior of the liquid-holding container can be similar to the shape of the substrate to be coated. In order to have the container with a shape similar to the substrate, the container can be molded to follow the shape of the substrate to be coated.

In one embodiment, the shape of the interior of the liquid-holding container is hemispheric and the substrate is a hip acetabular cap.

The liquid-holding container can optionally have a volume sufficient to allow a ratio of the aqueous system volume to the substrate surface area to be about 5 to about 50 mm.

The gas valve is a gas-releasing valve used to control the rate of release of a gas, such as carbon dioxide, from the liquid-holding container. The gas valve can be a manual gas valve, a pressure-responsive gas valve, or an automated gas valve.

Figure 6:
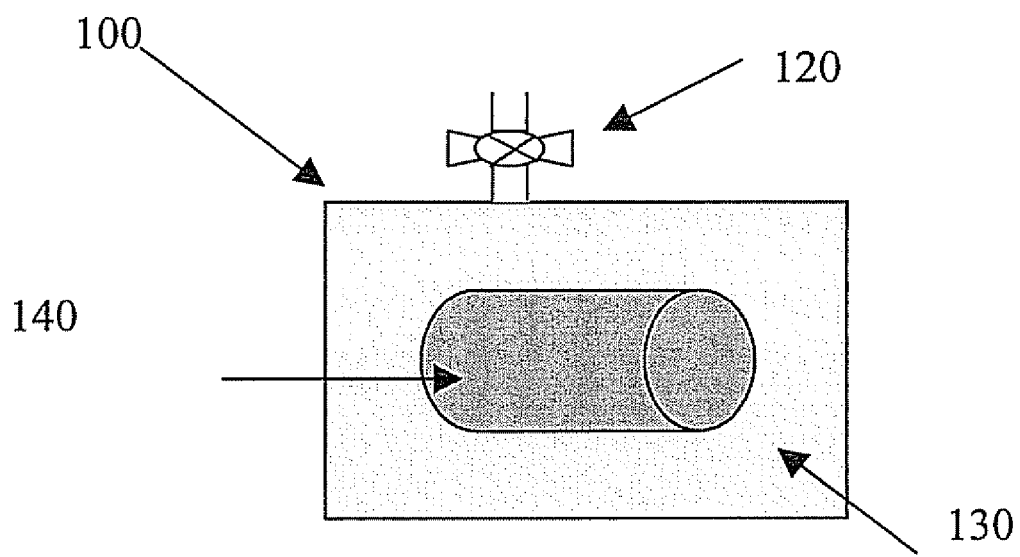
FIG. 6 is a schematic illustration of a general reactor used to produce coatings on irregular shaped substrates.

FIG. 6 is a schematic illustration of a general reactor used to produce coatings on irregular shaped substrates. In one embodiment, the reactor (100) for coating a substrate (140) with a ceramic coating containing a biologically active agent is a container with an aqueous system volume to substrate surface area ratio of 5 mm to 50 mm such that the coating achieves about 50% to about 100% incorporation efficiency for biologically active agent. The reactor (100) of FIG. 6 includes a gas valve (120) to control the $CO_2$ release rate from the aqueous system (130). The reactor container can be a double-jacketed container or it can be placed in an incubator to maintain a constant temperature in the container. With a suitable aqueous system volume to substrate surface area ratio and an appropriate $CO_3^-$ decomposition rate (or $CO_2$ release rate), which can be controlled by the gas valve, the decomposition of $HCO_3^-$ can be controlled to a point that only a trace amount of $HCO_3^-$ remains in the aqueous system after the apatite nucleation on the substrate surface. The coating formation process can be expedited due the depletion of the coating formation inhibitor ($HCO_3^-$).

Figure 7:
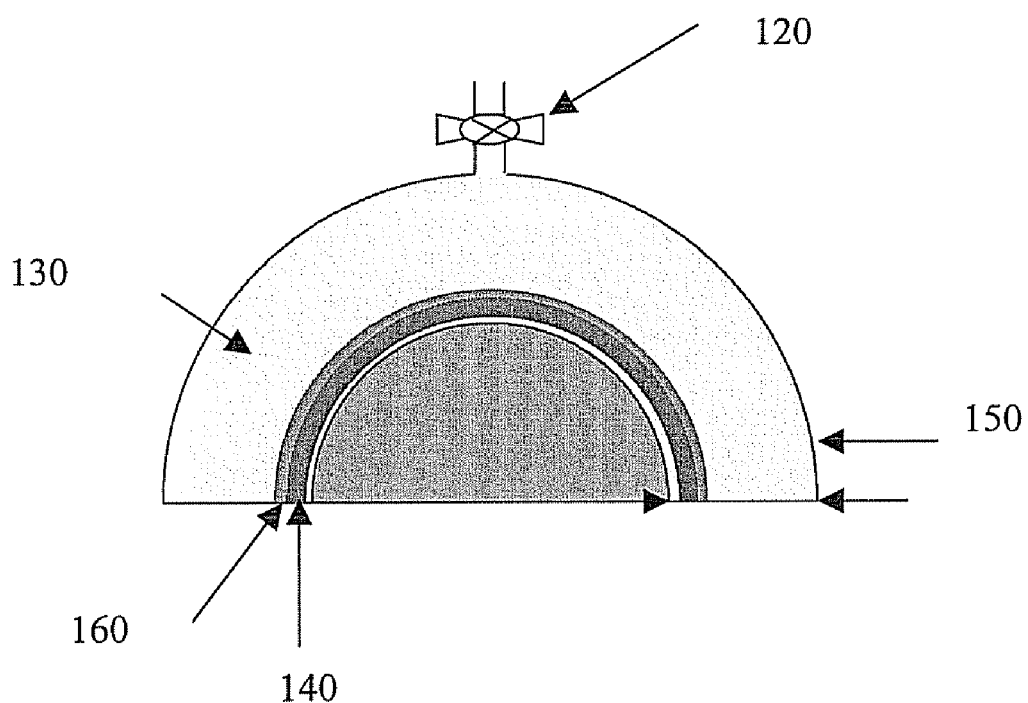
FIG. 7 is a schematic illustration of a reactor to produce a coating on the surface of a hip acetabular cap.

FIG. 7 is a schematic illustration of a reactor (150) to produce a coating (160) on the surface of a hip acetabular cap (140). The reactor (150) comprises of a reactor container (110) to house the aqueous system (130). Depending on the size of hip acetabular cap (140), the radius of the container internal chamber is about 5 to about 50 mm. The reactor also comprises a gas valve (120) to control the $CO_2$ release rate. The container can be either a cubic or hemisphere (as shown FIG. 7) which is similar to the shape of the hip acetabular cap such that the ratio of the aqueous system volume to the substrate surface area is 5 to 50 mm.

EXAMPLES

Example 1

Effect of the Temperature on the Calcium-Phosphate Coating Formation Process

A simulated body fluid (SBF) solution was prepared containing 7.5 millimolar (mM) $Ca^{2+}$, 3 mM $HPO_4^{2-}$, 142.0 mM $Na^+$, 5.0 mM $K^+$, 1.5 $Mg^{2+}$, 103.0 mM $Cl^-$, 27.0 mM $HCO_3^-$, and 0.5 mM $SO_4^{2-}$; prepared from NaCl, $NaHCO_3$, $Na_2CO_3$, KCl, $K_2HPO_4.3H_2O$, $MgCl_2.H_2O$, HEPES (11.928 g per 1000 mL water), $CaCl_2$, $Na_2SO_4$, and 1M HCl (6.5 mL per 1000 mL water). SLA® titanium discs provided by Straumann were used as the substrates in this study. The discs were sandblasted, gritted, and acid etched. The titanium discs were thoroughly washed with de-ionized water before immersion into the SBF solution. The formation of the coating was carried out at three different temperatures: 20° C., 40° C. and 60° C. After soaking the discs at each temperature for 24 hours (h), the discs were removed from the solution, gently washed using de-ionized water and dried at 60° C. in an oven overnight. The coatings were characterized using X-ray diffraction (XRD) and Fourier transform infra-red (FTIR) to determine the composition of the coating. Environmental electron scanning microscope (ESEM) was also used to examine the surface morphology of the coatings.

It was found that a calcium-phosphate coating having a reasonable thickness (about 10 to about 40 micrometers) was formed on the surfaces of the SLA discs under all three operating temperatures after only soaking in the SBF for 24 hours. XRD patterns of the calcium-phosphate coatings formed at different temperatures showed peaks between about 35 and 41 degree (θ) that are attributed to the substrate. At 20° C., except for the sharp peaks attributed to the titanium substrate, a "glass bulge" is present with no sharp peaks discernable, suggesting that the calcium-phosphate coating formed was an amorphous material. As the temperature increased to 40° C., a slight bulge, in combination with some peaks, was observed indicating a poorly crystallized calcium-phosphate coating was formed. The crystallinity of the coating improved with the increase of the temperature to 60° C., as a relatively crystallized calcium-phosphate coating was formed as evidenced by the XRD pattern.

It was found that the surface morphology of the coating also varied with the temperature of the coating step. ESEM images of the SLA titanium disc before and after coating at 20° C., 40° C., and 60° C. were obtained. It has been observed that the calcium-phosphate coatings were uniformly deposited on the surface of SLA discs. At a relatively low temperature, such as 20° C., the coating has a dense feature. When the temperature of the coating step was increased, the coating became increasingly porous.

As indicated by the results, bioactive ceramic coatings prepared from calcium-phosphate can be made on titanium substrates. The ceramic coating density/morphology and crystallinity can be tailored by the temperature of the coating step. Furthermore, a short deposition time was required to achieve a homogenous coating with a reasonable thickness.

Example 2

Preparation of a Bioactive Ceramic Coating Using an Aqueous System Stabilized with HEPES SLA® titanium discs available from Straumann were used as the substrates in this example. The discs were cleaned with deionized (DI) water prior to the coating process. An aqueous system used as the coat forming solution was prepared by dissolving 2.701 grams (g) of NaCl, 0.736 g of $NaHCO_3$, 0.112 g of KCl, 0.595 g of $K_2HPO_4.3H_2O$, 0.155 g of $MgCl_2.H_2O$, 24 g of HEPES, 0.733 g of $CaCl_2$ and 0.036 g of $Na_2SO_4$ in 500 milliliters (ml) of DI water. The initial pH of the aqueous system was adjusted to 6.40 by adding 0.5 ml of 1 molar (M) NaOH at room temperature (21° C.). The resulting aqueous system was clean and free of any visible precipitation.

A 100 ml aliquot of the aqueous system was transferred into a 200 ml Pyrex® glass bottle. Two SLA® titanium discs were added to two bottles. The bottles were then closed, capped, and placed into a temperature controlled water bath set at 40° C. The discs were soaked in the aqueous system for about 24 hours to effect coating formation. The coated SLA discs were then removed from the aqueous system, rinsed with DI water, and dried at room temperature.

Figure 2:
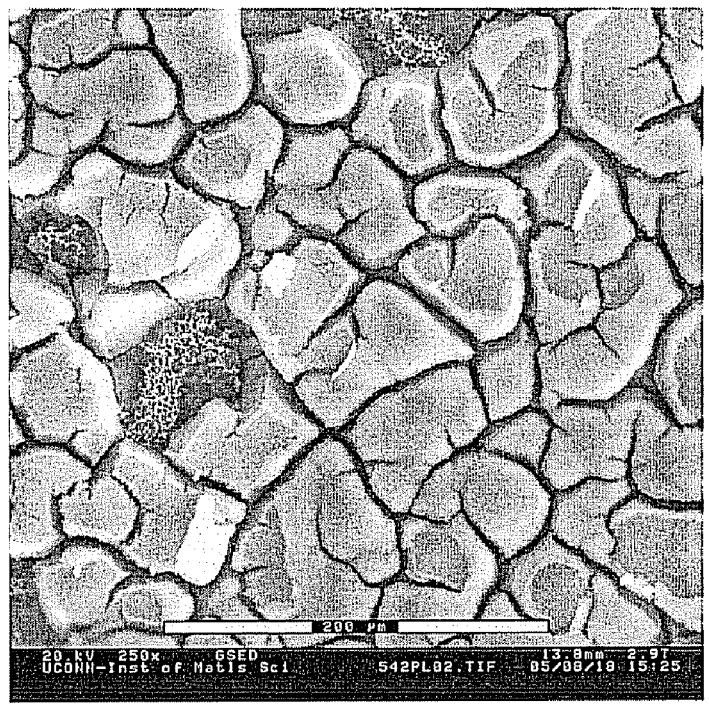
FIG. 2 illustrates an ESEM image of a coating surface closest to the substrate surface having a dense morphology.
Figure 3:
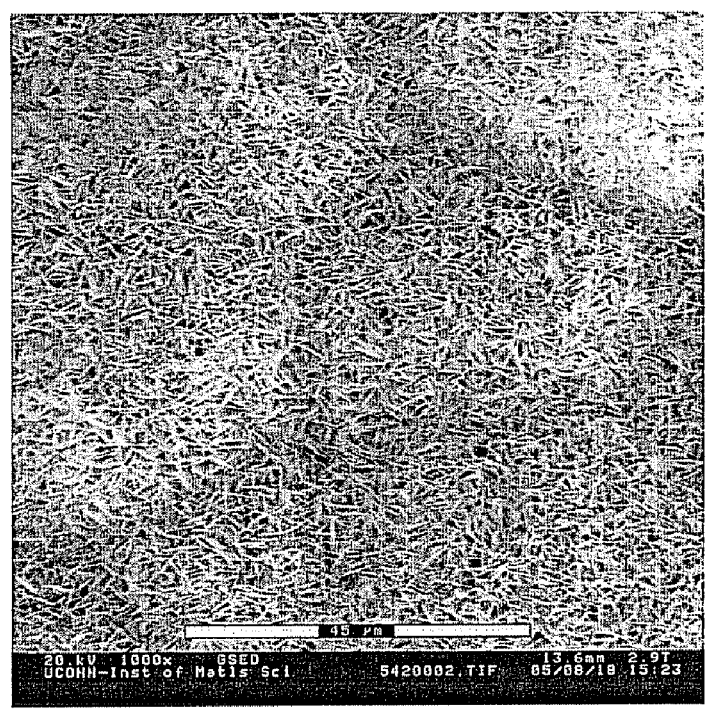
FIG. 3 illustrates an ESEM image of a coating surface furthest from the substrate having a less dense and more porous morphology.

The resulting coated discs were then characterized with XRD, FTIR, and ESEM. The analyses revealed a dense morphology to the coating nearest to the substrate surface (FIG. 2). The coating surface furthest from the substrate surface, however, was less dense and more porous (FIG. 3).

Example 3

Exploration of $NaHCO_3$ Concentration on the Morphology of the Resulting Ceramic Coating Aqueous systems having different $NaHCO_3$ concentration were tested to study the effect of the $HCO_3^-$ on the ceramic coating morphology. The amount of $NaHCO_3$ was varied as follows: 0.736 g of $NaHCO_3$ in 500 ml DI water and 1.472 g of $NaHCO_3$ in 500 ml DI water. The amounts of the remaining components were the same as described in Example 2 above, and the coating process was performed as described above for Example 2. It was determined that the solution containing 0.736 g of NaHCO$_3$ in 500 ml DI water was capable of forming a coating having a gradient morphology.

Example 4

Exploration of the Initial pH of the Aqueous System on the Morphology of the Resulting Ceramic Coating Aqueous systems having different initial pH were tested to study the effect on the ceramic coating morphology. The initial pH was varied as follows: 6.40, 6.46, and 6.52, each at room temperature (42° C.). The coating procedure and aqueous system were the same as described in Example 2 except that the initial pH of the system was adjusted. ESEM images were obtained showing that only the aqueous system having an initial pH at 6.40 formed a porous gradient coating.

A second experiment was performed exploring the initial pH of the aqueous system on the morphology of the resulting ceramic coating. The aqueous system according to Example 2 was used having a Ca$^{2+}$ ion concentration of 7.5 mM and an HPO$_4^{2-}$ ion concentration of 3.0 mM. Analytical grade reagents NaCl, NaHCO$_3$, MgCl$_2$, K$_2$HPO$_4$ and CaCl$_2$ were dissolved into de-ionized water with desired amounts. Hepes (4-(2-hydroxyethyl)-1-piperazineethanesulfonic acid) was chosen to buffer the solution. The concentrations of the remaining ions are provided in Table 1 below.

TABLE 1

| Ion | Aqueous system Ion concentration (mM) |
|---|---|
| Na$^+$ | 109.5 |
| K$^+$ | 6.0 |
| Mg$^{2+}$ | 1.5 |
| Ca$^{2+}$ | 7.5 |
| Cl$^-$ | 110.0 |
| HCO$_3^-$ | 17.5 |
| HPO$_4^{2-}$ | 3.0 |
| SO$_4^{2-}$ | 0 |

The aqueous systems were prepared having an initial pH of 6.56, 6.45 and 6.40, respectively, using addition of hydrochloric acid.

A commercially available titanium plate (McMaster-Carr) was cut into small plates with a size of 15×15×1 mm. These small plates were polished using a series of silicon carbide papers (grade 600-1200), and then rinsed with de-ionized water in an ultrasonic bath. The metal plates were dried at room temperature overnight. The clean titanium alloy plates were then soaked in 5 M NaOH solution at 60° C. for 3 days. After alkaline treatment, the titanium plates were gently cleaned with de-ionized water and immersed in 100 ml of each of the aqueous systems. The formation of the coating was carried out at a temperature of 40° C. After soaking for 24 hours, the plates were removed from each solution, gently washed and air-dried overnight. The pH value change in each aqueous system with the time was recorded using a pH meter (Accumet Excel XL15). The composition of the ceramic coating was evaluated using X-ray diffraction analysis (XRD) (BRUKER AXS D5005), and the surface morphology of the coating was observed using an environmental scanning electron microscopy (ESEM) (Philips ESEM 2020).

Figure 4:
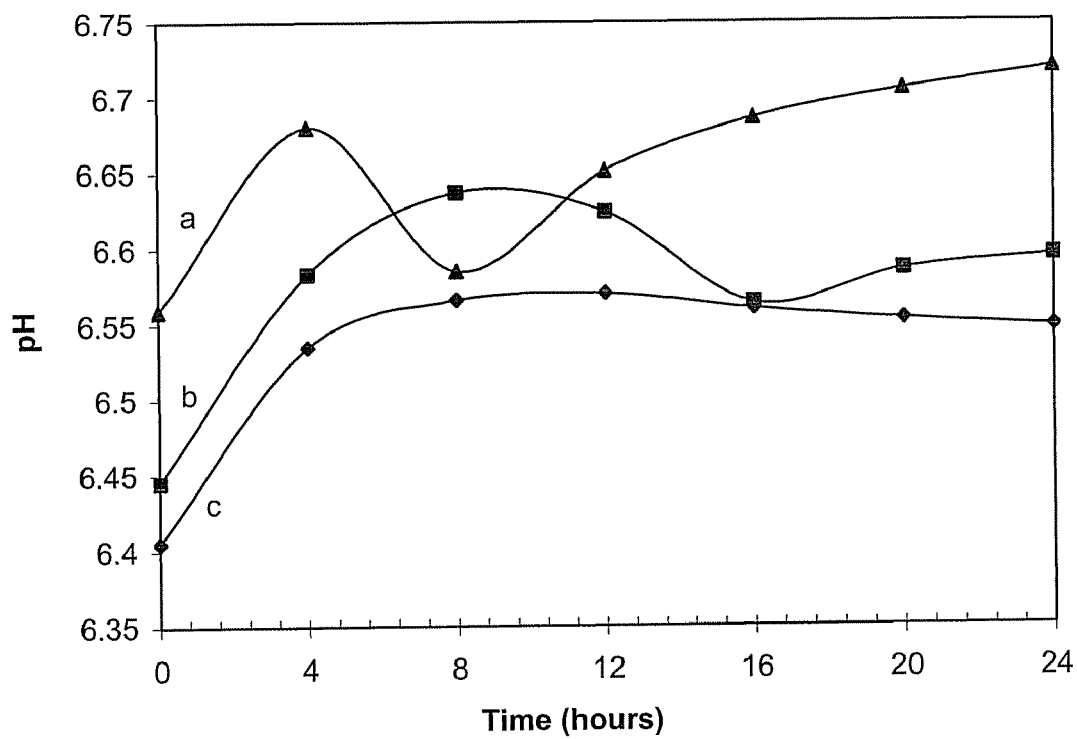
FIG. 4 illustrates pH versus time of immersion of the aqueous systems having an initial pH of a) 6.56, b) 6.45 and c) 6.40.

The aqueous system with the highest initial pH value, 6.56, started to form colloidal precipitates after 4 hours of soaking. The pH-time profile of this solution revealed that the pH value reached the peak (6.69) after 4 hours of immersing the specimen (FIG. 4). In contrast, the aqueous systems having an initial pH of 6.45 and 6.40 remained stable and clear throughout the experiment. The highest pH values of these two pH-time profiles were 6.64 and 6.55, respectively (FIG. 4). These results suggest that there is a pH range, above which the colloidal precipitation of apatite was yielded in the solution. The aqueous systems remained relative stable below this pH range.

ESEM images obtained showed that the ceramic coating was uniformly deposited on the surface of the titanium plates. The coating formed in the aqueous system having an initial pH of 6.45 was denser but with cracks, while the coating formed in the aqueous systems with initial pH values of 6.56 and 6.40 were rougher and more porous.

XRD results showed that pure apatite was formed at all three initial pH conditions. A broad peak around 31°-33° suggests that poorly crystallined apatite was formed for all three aqueous systems. The coating formed in the aqueous system with an initial pH of 6.56 had the lowest relative intensity (25°-27°, 31°-33°) to the substrate, while the coatings formed in aqueous systems with initial pH values of 6.45 and 6.40 had higher relative intensities. These results indicated that a relatively denser coating was formed for the aqueous system with a lower initial pH. Two chemical reactions occurred during the apatite formation in the aqueous system. First, both Ca$^{2+}$ and HPO$_4^{2-}$ ions reacted to form into apatite coatings at an appropriated pH range. Meanwhile, the bicarbonate ions (HCO$_3^-$) in the aqueous system decomposed into CO$_2$ and OH$^-$ and thereby increased the pH of the solution (HCO$_3^-$→CO$_2$+OH$^-$). The apatite coating forms when the aqueous system is within an appropriate pH range. When the pH of the solution is above the pH range (e.g., initial pH of 6.56), the apatite nucleates on the surface of the titanium substrates as well as in the aqueous system solution. As a result, less coating was generated on the surface of the substrate due to the competition between the two processes, as evidenced by the XRD results.

Due to the difference in initial pH values, the decomposition rate of the bicarbonate in the aqueous systems was different; therefore the remaining bicarbonate ion concentration in the aqueous systems was different. The higher the bicarbonate ion concentration in the aqueous system, the denser the coating formed. ESEM images revealed that the ceramic coating formed in an aqueous system with a lower initial pH (6.40) is more porous than the coating formed in an aqueous system with a higher initial pH (6.45). Without wishing to be bound by theory, these results are possibly due to the different bicarbonate ion concentrations in the solutions.

Example 5

Exploration of the Effect of Soaking Temperature on the Morphology of Ceramic Coating Aqueous systems having different soaking temperatures were tested to study the effect of temperature on the ceramic coating morphology. The coating procedure was the same as described in Example 2, but with varied soaking temperatures. The soaking temperatures explored were 20° C., 30° C., and 40° C. ESEM images showed that a gradient coating was formed at 40° C., while dense coatings were formed at lower temperatures.

Example 6

Exploration of the Effect of Aqueous System Volume on the Ceramic Coating Quality Aqueous systems having different volumes, (50, 100, and 200 ml), were employed to study the ceramic coating quality of the resulting ceramic coatings, particularly bonding strength between the coating and substrate. Commercially available titanium discs, 15 mm in diameter and 2 mm in thickness, were used as the substrates in this study. These discs were sandblasted, gritted and acid etched. They were thoroughly washed with de-ionized water before immersion in the aqueous systems. The aqueous system was prepared based on the procedure described in Example 2, where the $Ca^{2+}$ and $HPO_4^{2-}$ concentrations were adjusted to 12.5 mM and 5 mM, respectively. The aqueous system was buffered using 4-(2-hydroxyethyl)-1-piperazineethanesulfonic acid (HEPES), and the initial pH of the solution was adjusted using hydrochloric acid. The ion concentration of the resulting aqueous systems is provided in Table 2 below.

TABLE 2

| Ion | Aqueous system |
|---|---|
| $Na^+$ | 127.0 |
| $K^+$ | 10.0 |
| $Mg^{2+}$ | 3.0 |
| $Ca^{2+}$ | 12.5 |
| $Cl^-$ | 123.0 |
| $HCO_3^-$ | 35.0 |
| $HPO_4^{2-}$ | 5.0 |
| $SO_4^{2-}$ | 0 |

Three different volumes of the aqueous system, 50 ml, 100 ml or 200 ml, were placed in a 200 ml bottle to prepare type I, II and III apatite coatings, respectively. Substrate discs were added to each bottle and the bottles were sealed. The formation of the coating was carried out at a temperature of 40° C. After soaking in the aqueous system for 24 hours, the discs were removed from each solution, gently washed and air-dried for overnight.

Figure 5A:
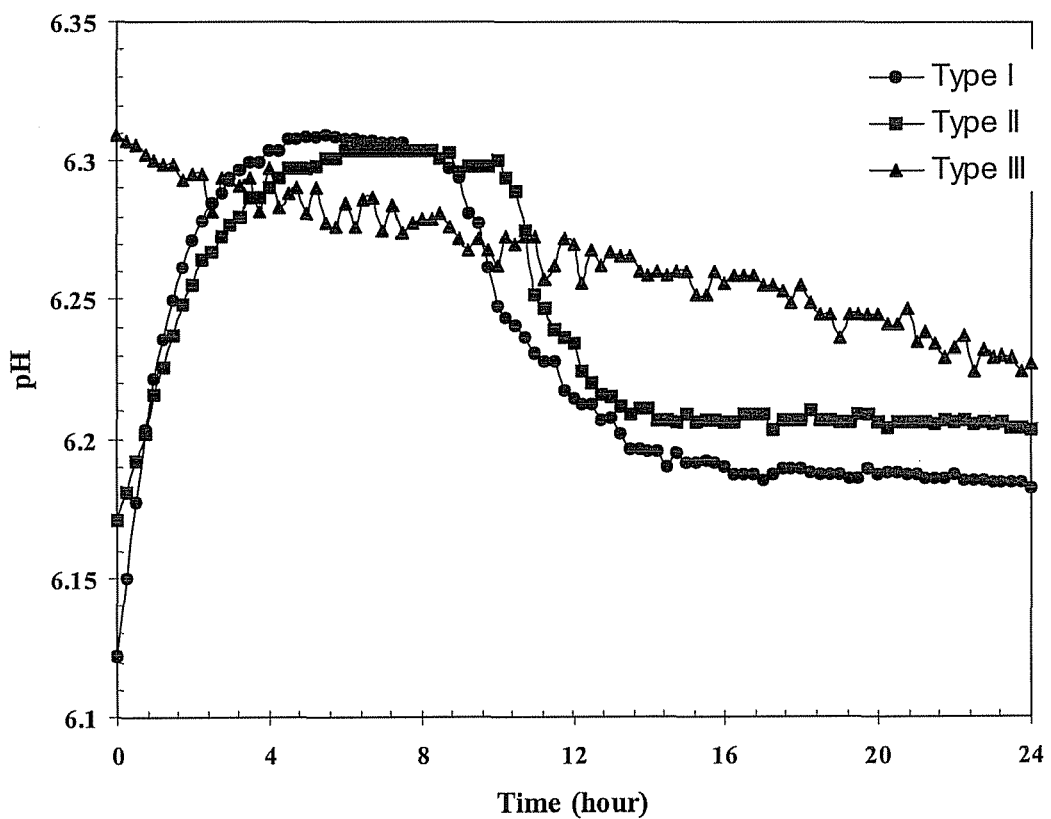
FIG. 5a illustrates pH versus immersion time of three volumes of aqueous system.

The change of pH with time in the three aqueous systems was measured using a pH meter (accumet Excel XL15). The pH of the solution was measured every 15 min, and a pH profile against time was plotted for the three solutions. The results are provided in FIG. 5a.

A two-stage pH profile was observed for the 50 ml aqueous system. At stage one, the pH of the 50 ml aqueous system increased at an initial rate of 0.075 pH unit/hour, and peaked at 4.5 hours. At stage two, the pH of the solution started to drop at 8 hours. Similarly, a two-stage pH profile was also observed for the 100 ml aqueous system. The pH of the solution increased at an initial rate of 0.040 pH unit/hour, peaked at 6-10 hours, and dropped afterwards. In contrast, a single stage pH profile was observed for the 200 ml aqueous system, where the pH of the solution dropped at an extremely low rate, 0.003 pH unit/hour, throughout the entire experiment.

The total inorganic carbon (TIC) content in the three aqueous systems before and after soaking the specimens was assessed using a total organic/inorganic carbon (TOC/TIC) analyzer (OI Analytical 700 TOC analyzer). Two soaking time points were studied, 12 and 24 hours, and each point was repeated 3 times. The results are provided in FIG. 5b.

Figure 5B:
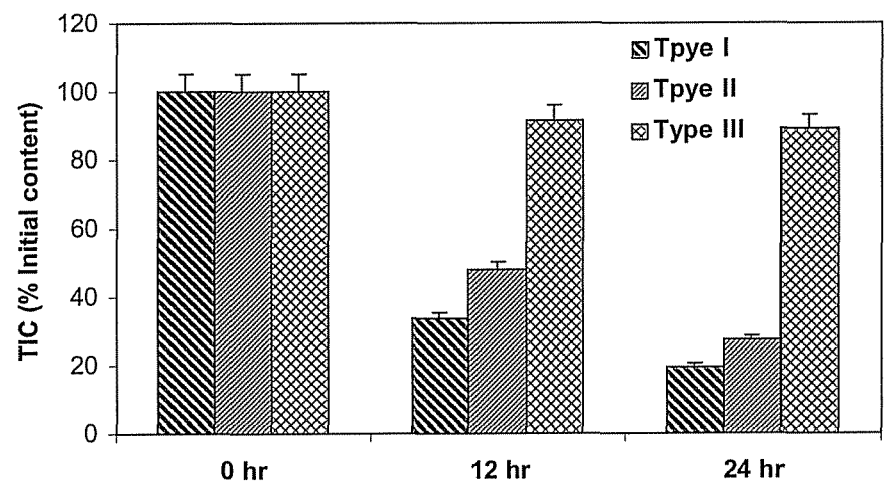
FIG. 5b is a graphic illustration of the total inorganic carbon (TIC) content in the three aqueous systems of varying volumes before and after soaking the substrates.

The carbonate/bicarbonate ion content in all three aqueous systems at different time points was measured using a total inorganic carbon analysis. The TIC measurement revealed that the carbonate/bicarbonate ions decreased with the increase of the soaking time for both the 50 ml and the 100 ml aqueous systems during the coating formation (FIG. 5b). In the first 12 hours, approximately 70% and 50% of carbonate/bicarbonate ions were released from the 50 ml and the 100 ml aqueous systems, respectively. After 24 hours of reaction, about 80% and 70% of the carbonate/bicarbonate ions were released from the 50 ml and the 100 ml aqueous systems, respectively. In contrast, the TIC content varied little during the entire coating process for the 200 ml aqueous system.

The amount of coating was determined using the following procedure. Coating was formed on both sides of titanium substrates. The bottom side of the apatite coating was gently removed using hydrochloric acid. After being dipped into 1M HCl, a cotton Q-tip was used to gently nib across the coating to dissolve the apatite coating. The substrates were then cleaned with DI water and dried at room temperature. After the bottom side of the coating was removed, each of the top coating was also removed by dissolving in 10 ml 1M HCl solution for 10 min. The weight of the top coating was calculated as the difference between the weight of the substrates before and after removing the coating.

The coatings were examined using X-ray diffractometer (BRUKER AXS D5005) with a copper target. The voltage and current setup were 40 kV and 40 mA, respectively. A step size of 0.02° and a scan speed of 0.5°/min were used. The XRD pattern of the coatings prepared from the 50 ml, 100 ml, and 200 ml aqueous systems suggest that pure apatite coatings were obtained for all systems. The bulge at around 31°-33° (an overlap of 3 major peaks ((211), (112) and (300) of hydroxyapatite) suggests that poorly crystallined apatite was formed for all three coating systems. The relative intensity of this bulge (31°-33°) increased as the aqueous system volume increased, and the highest density was observed for the 200 ml aqueous system.

The coating thickness and surface morphology of the apatite coatings was evaluated using an environmental scanning electron microscope (ESEM) (ESEM 2020 Philips). The densities of different types of coatings were also evaluated using weight and thickness of the top coatings. ESEM images indicate that uniform ceramic coatings were formed on titanium discs for all three aqueous systems, yet the coating morphologies were different. The coating obtained from the 50 ml aqueous system (type I) was the least dense, crack-free, and uniformly composed of numerous apatite globules of 30-50 μm in diameter. The coating obtained from the 100 ml aqueous system (type II) was denser than type I coating, and its apatite globules had a much smaller size, 20-30 μm in diameter. The coating obtained from the 200 ml aqueous system (type III) was the densest among the three coatings. The size of apatite globules on type III apatite coating was the smallest, 10-20 μm in diameter. The properties of weight, thickness, and average density of the three types of coatings are provided in Table 3. As illustrated, by increasing the volume of the aqueous system, the three parameters of weight, thickness, and density are all increased.

TABLE 3

| | Coating | | |
|---|---|---|---|
| Property | Type I | Type II | Type III |
| Weight (mg) | 4.5 | 8.5 | 11.5 |
| Thickness (μm) | 12 ± 2 | 19 ± 1 | 24 ± 3 |
| Density (% of Theoretical density) (d = weigh/(thickness * surface area) | 67% | 80% | 85% |

The bonding strength of the three types of apatite coatings to the substrates was evaluated using a modified ASTM C-633 method as provided in Kim H-M, Miyaji F, Kokubo T, Nakamura T. "Bonding strength of bonelike apatite layer to Ti metal substrate." *Journal of Biomedical Materials Research* 1997; 38(2):121-127. Both sides of the substrates (with apatite coating on one side) were bonded to a cylindrical stainless steel fixture (15 mm in diameter and 15 mm in length) using a super-glue (Henkel, Loctite Superglue, USA). The tensile load was applied normal to the substrates using al Instron testing machine (Instron 5869) at a crosshead speed of 1 mm/min until fracture occurred. For each type of coating, five specimens were tested. The fracture surface of the specimens was examined using an environmental scanning electron microscope (ESEM) (Philips ESEM 2020).

The average bonding strength for the three aqueous systems using the tensile strength test were 8.52±2.41, 10.36±2.78 and 17.23±2.55 MPa for types I, II, and III apatite coatings, respectively. The average bonding strength of type I coating was slightly lower than that of type II coating, although the difference was not significant. In contrast, the bonding strength of type III coating was significantly higher than those of both types I and II coatings (p<0.01).

ESEM images showed the fracture surface of substrate and the attached fixture for all apatite coatings. No glue penetration was observed for all coating systems. Apatite was observed on the surfaces of both the substrate and the fixture for all three types of apatite coatings. However, the amount of apatite observed on the substrate decreased in the following order: type I>type II>type III. This suggested that the bonding strength within the apatite coating became stronger with the increase of the aqueous system volume, and the coating became less and less likely to fail cohesively within the apatite coating. For type I and II coatings, the ESEM images exhibited that most of the fractures occurred within the apatite coating. While for type III coating, most of the fractures occurred at the interface between the coating and substrate. When titanium substrates were soaked in the aqueous system, two chemical reactions occurred during the apatite coating formation process. First, both $Ca^{2+}$ and $HPO_4^{2-}$ ions were adsorbed onto the surface of the substrate to form into apatite coatings. During the further growth of the apatite coating, the pH of the solution decreased due to $H^+$ release or $OH^-$ consumption according to the general reaction $5Ca^{2+}+3HPO_4^{2-}+4OH^-\rightarrow Ca_5(PO_4)_3OH+H_2O$ (equation (1)). In addition, the bicarbonate ions ($HCO_3^-$) in the solution decomposed into $CO_2$ and $OH^-$, as shown in equation $HCO_3^-\rightarrow CO_2+OH^-$ (equation (2)), increasing the pH of the aqueous system.

In general, the apatite coating forms when the aqueous system is within an appropriate pH range. When apatite is formed, the pH of the aqueous system decreases, as shown in equation (1). To have continuous apatite formation, the pH of the aqueous system can be increased by the decomposition of $HCO_3^-$, as shown in equation (2). Not wishing to be bound by theory, but the coating formation process is controlled by the decomposition of $HCO_3^-$ which decomposes at different rates depending upon the headspace volume in the closed system. Both types I and II aqueous systems demonstrated a two-stage pH profile. At the first stage, the pH of the solution was increased to the pH range for apatite formation by the decomposition of $HCO_3^-$. According to Henry's Law the amount of $CO_2$ in the aqueous system is in direct proportion to the partial pressure of the $CO_2$ above the aqueous system in the sealed container. In this study, three different volumes of aqueous system were used with the following order: $Vt_{typeI}<V_{typeII}<V_{typeIII}$. The lower the volume of the aqueous system, the higher the volume of the air in the headspace of the sealed container, and the more $CO_2$ is needed to build up a high $CO_2$ partial pressure in the sealed container. In this study, the type I system (50 ml aqueous system) had the largest space above aqueous system among the three systems.

As a result, more $CO_2$ was expected to release from the type I solution than type II solutions before the $CO_2$ partial pressure in the space above the aqueous system reached equilibrium. The TIC results support the above assumptions. It was found that after 12 hours, only about 30% and 50% carbonate/bicarbonate ions remained in the types I and II aqueous systems, respectively. Further, based on Henry's Law and equation (2), a more rapid pH increase at stage I was shown for type I solution than that of type II as more $CO_2$ released from the type I solution. The pH profile of these two solutions showed that it took less time (4-5 hours) for type I solution to reach the peak pH value than type II solution (6 hours). In addition, the total pH increase (0.19 unit) at the first stage for type I solution was higher than that for type II solution (0.13 unit). Due to faster pH increase at the first stage of type I solution, a relatively lower initial pH was introduced for this system to avoid the pH overshot at the peak range. At the second stage, the pH of both types I and II solutions decreased. A pH decrease was also observed for type III solution from the beginning to the end. The pH decrease suggests that more $OH^-$ ions were consumed to form apatite than those decomposed by $HCO_3^-$. Unlike the sharp pH drop in both types I and II solutions after reaching the peak points, the pH of type III solution decreased very slowly throughout the whole experiment. The TIC result indicated that there was more than 95% carbonate/bicarbonate ions remained in the type III solution after 24 hours, while only about 20% and 30% carbonate/bicarbonate ions remained in type I and type II solutions, respectively. The combination of the TIC results and pH profiles suggest that the pH change in type III solution is attributed to the apatite formation.

Besides $HCO_3^-$ decomposition, $HCO_3^-$ itself can also affect apatite formation. The carbonate in the aqueous system can contribute to the formation of carbonated apatite, and the high $HCO_3^-$ content could render a dense apatite coating. Not wishing to be bound by theory, the combination of the above two factors suggest that the apatite coating becomes more porous with the decrease of the $HCO_3^-$ content in the aqueous system. The $HCO_3^-$ content in the three aqueous systems increased in the order of type I<type II<type III, and the density of apatite coating formed on the titanium substrates increased in the order of aqueous system volume: type III (85%)>type II (80%)>type I (67%) (Table 3). Also the surface morphology of apatite coatings revealed that the coatings were getting denser as aqueous system volume increased. Accordingly, it can be concluded from the results of density and morphology of the apatite coatings that the apatite coating grew denser as the aqueous system volume increased.

The volume of aqueous system also affects the bonding strength of the apatite coating. Most of the type I and II coatings failed within the apatite coating, suggesting the cohesive strength within the coating (8-10 MPa) was lower than the bonding strength at the interface between the coating and the substrate. In contrast, most of the type III coating failed at the interface between the coating and the substrate, indicating that the cohesive strength within the coating was stronger than the interfacial bonding strength, about 17 MPa. Based on the examination of the failure sites and the bonding strength of different types of apatite coatings, the bonding strength of the coating could be significantly improved by reducing the rate of coating formation to form a dense coating.

Example 7

Exploration of the Effect of the Ratio of Solution Volume to the Substrate Surface Area on the Coating Formation Process A simulated body fluid solution was prepared containing 7.5 millimolar (mM) $Ca^{2+}$, 3 mM $HPO_4^{2-}$, 142.0 mM $Na^+$, 5.0 mM K$^+$, 1.5 Mg$^{2+}$, 103.0 mM Cl$^-$, 27.0 mM HCO$_3^-$, and 0.5 mM SO$_4^{2-}$; prepared from NaCl, NaHCO$_3$, Na$_2$CO$_3$, KCl, K$_2$HPO$_4$.3H$_2$O, MgCl$_2$.H$_2$O, HEPES (11.928 g per 1000 mL water), CaCl$_2$, Na$_2$SO$_4$, and 1M HCl (6-10 mL per 1000 mL water). High-grade titanium plates (7 mm×7 mm) were cleaned with ethanol and de-ionized water. The titanium plates were then soaked in 5M NaOH solution at 60° C. for 3 days. The titanium plates were thoroughly washed with de-ionized water before immersion into the aqueous system. The formation of the coating was carried out at three different volumes: 0.5, 1.5 or 2.5 ml in a 7.5 ml vial (the ratio of aqueous system volume to the plate surface area is 10 mm, 20 mm and 30 mm, respectively). After soaking in the aqueous system for 24 hours at 40° C., the plates were removed from the aqueous system, gently washed (rinsed) for about two minutes at room temperature using about 500 ml of de-ionized water and dried at room temperature for overnight. Both of the amount of calcium left in the aqueous system and the amount of calcium that incorporated into the coating were measured using atomic absorption spectrophotometry (AAS). Environmental electron scanning microscope (ESEM) was used to examine the surface morphology of the coatings.

It was found that the surface morphology of the coating, and the calcium and phosphate incorporation rate varied with the volume of the aqueous system. ESEM images showed that at a low volume solution, such as 0.5 ml, the coating had a porous feature. When the volume of the solution increased, the coating became increasingly dense. With larger aqueous system volume, it took a longer time for the HCO$_3^-$ to completely decompose. Therefore more HCO$_3^-$ remained in the solution and, as a result, slowed down the apatite formation. Calcium and phosphate measurements revealed that increasingly more calcium and phosphate had contributed to the formation of apatite coating as the aqueous system volume decreased. Table 4 provides the aqueous system volume effect on calcium and phosphate incorporation efficiency.

TABLE 4

| Solution | Coating | | |
|---|---|---|---|
| | 0.5 ml | 1.5 ml | 2.5 ml |
| Ratio of solution volume to the plate surface area | 10 mm | 30 mm | 50 mm |
| % Phosphate incorporated | about 100 | 84.5 | 63.2 |
| % Calcium incorporated* | about 67 | 60.1 | 48.9 |

*Note:
The stoichiometric Ca:P ratio of hydroxyapatite is 1.67 while the Ca:P ratio of the aqueous system is 2.5. Therefore the maximum calcium incorporation efficiency of the aqueous system is around 67%.

Example 8

Exploration of the Initial pH of the Aqueous System on the Morphology of the Resulting Ceramic Coating Aqueous systems having different initial pH were tested to study the effect of pH on the ceramic coating morphology. The initial pH was varied as follows: 6.20, 6.31, 6.40, 6.52, each at room temperature (23° C.). The ratio of solution volume to the plate surface area was 10 mm. The coating procedure and aqueous system were the same as described in Example 7 except that the initial pH of the system was varied. The aqueous system having initial pHs at 6.20 and 6.31 formed coating without precipitation. Such precipitations are the result of nucleation of hydroxyapatite in solution rather than on the substrate surface. The precipitation in the solution is undesirable as a large amount of the biologically active agent can remain in the solution by absorbing to the precipitations in the solution instead of incorporating into the coating on the substrate. As a result, the incorporation efficiency of the biologically active agents in such systems is low.

Example 9

Exploration of the Effect of Biologically Active Agent Concentration on Biologically Active Agent Incorporation Efficiency Aqueous systems with different concentrations of bovine serum albumin (BSA) were used to study the biologically active agent incorporation efficiency. The BSA concentration was varied as follows: 0.1 mg/ml, 0.01 mg/ml, 0.001 mg/ml and 0.0001 mg/ml. The formation of the coating was carried out by adding 0.5 ml of the aqueous system in a 7.5 ml vial with an initial pH of 6.20 at 40° C. for 24 hours. The aqueous system and coating procedures were the same as described in Example 8. Coatings were formed for all systems. Table 5 illustrates the incorporation efficiency of BSA with different initial BSA concentrations. The results show that almost all BSA (>85%) was incorporated into the ceramic coating. The BSA concentration that can be achieved is about 40 μg/cm$^2$. It has been reported that bone morphogenetic protein (BMP) concentration over 250 μg/implant can significantly improve the bone growth of primate (baboon and monkey). Therefore, in order to achieve a medically useful level of BMP concentration, only small amounts (about 6-7 ug/cm$^2$ coating) would be needed.

TABLE 5

| | Coating | | | |
|---|---|---|---|---|
| Solution | 0.1 mg/ml | 0.01 mg/ml | 0.001 mg/ml | 0.0001 mg/ml |
| Initial BSA concentration (μg/cm$^2$) | 40 | 5 | 0.5 | 0.05 |
| % BSA incorporated | 85 | about 100 | about 100 | about 100 |

Example 10

Exploration of the Effect of Aqueous System Volume on Biologically Active Agent Incorporation Efficiency Commercially available titanium plates (20 mm×20 mm×1 mm) were used as the substrates. The plates were sandblasted with 800# sand paper, gritted and then treated with 5M NaOH at 60° C. for 24 h. The plates were thoroughly washed with de-ionized water before immersion in the aqueous system.

The aqueous system was prepared according to Example 7 above wherein the Ca$^{2+}$ and HPO$_4^{2-}$ concentrations of the solution were adjusted to 7.5 mM and 3.0 mM, respectively. Aliquots of the aqueous system were placed in sealed 40 ml bottles to prepare solutions containing BSA. The pretreated titanium plates were horizontally placed within individual beakers containing 3 mL of the aqueous system and Fluorescein-isothiocyanate (FITC)-labeled BSA (FITC-BSA) (Fraction V, >98%, Sigma, USA) at 100 μg/ml (n=4). Samples were incubated in a water bath, maintained at 42° C. for 24 hours.

The coated plates were then rinsed with de-ionized water and air dried at ambient temperature.

FESEM micrographs of the coated plates containing the FITC-BSA were compared to a coated plate free of FITC-BSA (control). Both the coatings with and without BSA were composed of crystals of about 0.3 µm thick and 2 µm across, but the shapes of the crystal plates of the two kinds of coatings were quite different. The observed differences between the two kinds of coatings indicate that not only is BSA absorbed to the surface of the coating, but also affects the lattice structure and orientation of crystals of the coating.

To visualize the spatial distribution of FITC-BSA in the coating, FITC-BSA incorporated coatings were compared with a non-protein coating (negative control) using confocal microscopy (Leica SP2 Spectral Confocal Microscope) at an excitation wavelength of 488 nm using a 40× magnification oil immersion. A side depth profile through the thickness of the mineral layer on each of the coatings was obtained by stacking the series of images. Results indicate that the BSA incorporated into the coating distributed homogeneously through the whole thickness of the coating.

The amount of FITC-BSA in the coating was determined using an indirect method: the aqueous systems remaining after the coating processes were collected and the concentrations of FITC-BSA were measured by a microplate reader (Molecular Devices M2 plate reader) with a fluorescence absorbance mode: Ex: 490 nm; Em: 530. The concentrations of FITC-BSA in the aqueous systems before the coating process were also measured. A calculation was then performed to compute the incorporation rate of BSA into the coatings:

$$R_{incorporation}(\%)=(C_{total}-C_{remaining})/C_{total}\times 100\%$$

$R_{incorporation}$: FITC-BSA incorporation rate into coating
$C_{total}$: FITC-BSA concentration in the aqueous system before coating
$C_{remaining}$: FITC-BSA concentration remaining in the aqueous system after coating For the aqueous system with a BSA concentration of 100 µg/ml, about 76% BSA incorporated into the coating. This result suggests that a high incorporation rate can be achieved using biomimetic co-precipitation. The high incorporation rate of BSA into the coating was due to the smaller volume of aqueous system used in this study.

Calcium and phosphate remaining in the aqueous system after the coating process were quantified to calculate the incorporation rate of Calcium and Phosphate, respectively. Calcium concentrations were measured by atomic absorbance spectromatography (AAS); phosphate concentrations were obtained by molybdenum blue chemistry method: a reagent of pure water, 2.5% ammonium molybdate reagent, 10% wt ascorbic acid (v:v:v=5:1:1) was prepared by orderly adding in all the components; the samples were mixed with the reagent by 1:4 (v/v) then incubated in 60° C. water bath for 15 min.; all the samples were measured under a microplate reader (Biotek, MQX200) under a wavelength of 830 nm. A simple calculation was performed to compute the incorporation rate of calcium and phosphate into the coatings:

$$R_{Incorporation}(\%)=(C_{total}-C_{remaining})/C_{total}\times 100\%$$

$R_{incorporation}$: calcium or phosphate incorporation rate into coating
$C_{total}$: calcium or phosphate concentration in the aqueous system before coating
$C_{remaining}$: calcium or phosphate concentration remaining in the aqueous system after coating Calcium and phosphate incorporation rate of the examined aqueous system were relatively high. The phosphate incorporation rate was around 90% which meant that most of phosphate in the aqueous system had been consumed for the formation of the coating. Compared to phosphate, the incorporation rate of calcium was about 60%. The lower rate is believed to be due to the high initial calcium ion concentrations in the aqueous system. The remaining calcium in the aqueous system would not decrease after the phosphate was almost used up to form the coating.

To characterize the protein release kinetics, the coated titanium plates were soaked in 3 ml of phosphate buffered saline (PBS) at pH=7.4 in sealed beakers in a 37° C. incubator. At certain time intervals, 3 ml of the immersion solution was taken out for FITC-BSA concentration measurement. The same volume of fresh PBS was refilled into the beaker at each time point. The FITC-BSA concentration was measured as previously described.

Figure 8:
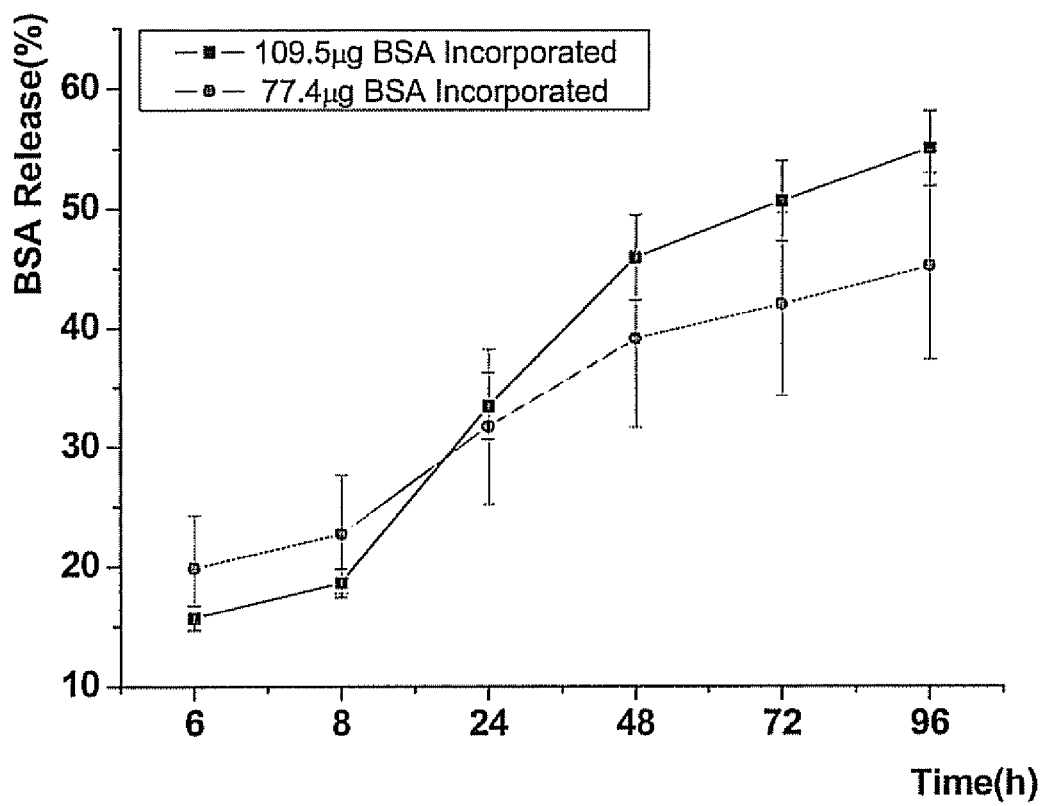
FIG. 8 biologically active agent release behavior from apatite coating.

The results of the release analysis reveals that the incorporated BSA was gradually released as a function of soaking time. Two release stages were observed, as shown in FIG. 8. An initial burst release of BSA was observed during the first 48 hours, whereas a sustained release was demonstrated for the following 48 h. After 96 hours of release study, 55% of the BSA had released from the coating for the system with an initial dose of 109.5 µg BSA, while 45% BSA was released for the system with an initial dose of 77.4 µg. These results show a high BSA release rate compared to the results reported by other researchers.

The terms "a" and "an" herein do not denote a limitation of quantity, but rather denote the presence of at least one of the referenced item. The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 wt %, or, more specifically, about 5 wt % to about 20 wt %", is inclusive of the endpoints and all intermediate values of the ranges of "about 5 wt % to about 25 wt %," etc).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A coated substrate, comprising:
    a gradient ceramic coating, wherein the gradient ceramic coating is prepared by exposing a portion of a substrate to an aqueous system, wherein the exposing is performed at a temperature of about 20° C. to about 100° C.;
    wherein the aqueous system comprises water, Ca2+, Mg2+, Na+, K+, Cl—, SO42-, HPO42-, HCO3- and a buffer system; and
    wherein the aqueous system has an initial pH of about 5.5 to about 7.5; and
    the gradient ceramic coating has a density of about 75 to about 90% closest to the substrate and a density of about 35 to about 60% at the gradient ceramic coating surface as determined by scanning electron microscope.

2. The coated substrate of claim 1, wherein the buffer system comprises 4-(2-hydroxyethyl)-1-piperazineethanesulfonic acid, 4-(2-hydroxyethyl)-1-piperazineethanesulfonic acid salts, tris-hydroxymethyl aminomethan, piperazine-1,4-bis(2-ethanesulfonic acid), piperazine-1,4-bis(2-ethanesulfonic acid) salts, or combinations thereof.

3. The coated substrate of claim 1, wherein the gradient ceramic coating has a total thickness of about 5 micrometers to about 50 micrometers.

4. The coated substrate of claim 1, wherein the coated substrate is an implantable medical device.

5. A coated substrate, comprising:
   a ceramic coating comprising a biologically active agent, wherein the ceramic coating is prepared by exposing a portion of a substrate to an aqueous system, wherein the exposing is performed at a temperature of about 20° C. to about 100° C.;
   wherein the aqueous system comprises water, $Ca^{2+}$, $Mg^{2+}$, $Na^+$, $K^+$, $Cl^-$, $SO_4^{2-}$, $HPO_4^{2-}$, $HCO_3^-$, a buffer system and a biologically active agent; and
   wherein the aqueous system has an initial pH of about 5.5 to about 7.5,
   wherein during the exposing, a ratio of aqueous system volume to substrate surface area is about 1 mm to about 50 mm.

6. The coated substrate of claim 5, wherein the buffer system comprises 4-(2-hydroxyethyl)-1-piperazineethanesulfonic acid, 4-(2-hydroxyethyl)-1-piperazineethanesulfonic acid salts, tris-hydroxymethyl aminomethan, piperazine-1,4-bis(2-ethanesulfonic acid), piperazine-1,4-bis(2-ethanesulfonic acid) salts, or combinations thereof.

7. The coated substrate of claim 5, wherein the following are present in the aqueous system:
   $Ca^{2+}$ is present in an amount of about 2.5 to about 15.0 mM;
   $Mg^{2+}$ is present in an amount of about 0.5 to about 5.0 mM;
   $Na^+$ is present in an amount of about 50.0 to about 300.0 mM;
   $K^+$ is present in an amount of about 2.0 to about 20.0 mM;
   $Cl^-$ is present in an amount of about 50.0 to about 350.0 mM;
   $SO_4^{2-}$ is present in an amount of about 0 to about 2.0 mM;
   $HPO_4^{2-}$ is present in an amount of about 1.0 to about 10.0 mM; and
   $HCO_3^-$ is present in an amount of about 10.0 to about 150.0 mM.

8. The coated substrate of claim 5, wherein the coated substrate is an implantable medical device.

9. The coated substrate of claim 7, wherein the initial pH of the aqueous system is about 6.20 to about 6.38.

10. The coated substrate of claim 5, wherein the incorporation efficiency of the biologically active agent in the coating is about 50 to about 100%.

11. The coated substrate of claim 5, wherein the ratio of aqueous system volume to substrate surface area is about 10 mm to about 40 mm.

* * * * *